United States Patent
Bruns et al.

(10) Patent No.: US 7,884,118 B2
(45) Date of Patent: Feb. 8, 2011

(54) 1-CYCLOALKYL-5-IODOTETRAZOLES

(75) Inventors: Rainer Bruns, Leverkusen (DE);
Martin Kugler, Leichlingen (DE);
Erasmus Vogl, Leverkusen (DE);
Hermann Uhr, Leverkusen (DE);
Oliver Kretschik, Pittsburgh, PA (US)

(73) Assignee: LANXESS Deutschland GmbH, Leverkusen (DE)

( * ) Notice: Subject to any disclaimer, the term of this patent is extended or adjusted under 35 U.S.C. 154(b) by 146 days.

(21) Appl. No.: 11/922,426

(22) PCT Filed: Jun. 27, 2006

(86) PCT No.: PCT/EP2006/006182
§ 371 (c)(1),
(2), (4) Date: Aug. 5, 2008

(87) PCT Pub. No.: WO2007/025586
PCT Pub. Date: Mar. 8, 2007

(65) Prior Publication Data
US 2009/0042960 A1    Feb. 12, 2009

(30) Foreign Application Priority Data
Jul. 9, 2005    (DE) .................. 10 2005 032 209

(51) Int. Cl.
*A61K 31/41*    (2006.01)
*C07D 257/04*    (2006.01)
(52) U.S. Cl. ..................................... 514/381; 548/251
(58) Field of Classification Search ............... 548/250, 548/251; 514/381
See application file for complete search history.

(56) References Cited
U.S. PATENT DOCUMENTS
4,786,311 A    11/1988    Levitt ........................... 71/90

FOREIGN PATENT DOCUMENTS
WO    2006/012996    2/2006

OTHER PUBLICATIONS

Copending U.S. Appl. No. 11/658,202, filed 2007.*
Jacobson, et al., J.O.C., 1954, vol. 19, pp. 1652-1661.*
R. Rapp, Can. J. Chem. 1971, 49, 2139-2142 "Reactions of 1-Substituted 5-Tetrazolyllithium Compounds; Preparation of 5-Substituted 1-Methyltetrazoles."
Satoh, Yoshitaka; Tetrahedron Lett., 1995, vol. 36, No. 11, 1759-1762 "Application of 5-Lithiotetrazoles in Organic Synthesis".
Satoh, Yoshitaka et al, Synlett 1998, 528-530 Homologation of 1-(Benzyloxymethyl)-1*H*-tetrazole Via Lithiation.
P.N. Gaponik, Khimiya Geterotsiklicheskikh Soedinenii 1988, 1699 (Abstract Attached).
Science of Synthesis, vol 13.30 Tetrazoles, p. 864, 2004.
Brigas A F ed—Bellus D (ED): "Product Class 30: Tetrazoles" Science of Synthesis. Category 2: Hetarenes and Related Ring Systems Five Membered Hetarenes With Three of More Heteroatoms, Methods of Molecular Transformations. (Houben-Weyl), Stuttgart: Georg Thieme Verlag, DE, Bd. vol. 13, 2004, Seiten 861-915, XP008068414 ISBN: 3-13-112281-1 das ganze dokument.

* cited by examiner

*Primary Examiner*—Joseph R Kosack
*Assistant Examiner*—Matthew P Coughlin
(74) *Attorney, Agent, or Firm*—Nicanor A. Kohncke

(57) ABSTRACT

The compounds of the formula (I)

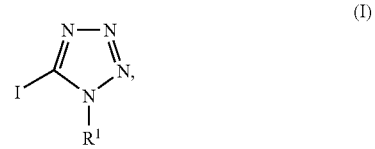

in which
$R^1$ represents cycloalkyl,
and its stereoisomers and any mixtures thereof are highly suitable as microbicides for protecting plants and materials.

10 Claims, No Drawings

1-CYCLOALKYL-5-IODOTETRAZOLES

CROSS REFERENCE TO RELATED PATENT APPLICATIONS

The present patent application claims the right of priority under 35 U.S.C. §119 (a)-(d) and 35 U.S.C. §365 of International Application No. PCT/EP2005/007824, filed 19 Jul. 2005, which was published in German as International Patent Publication No. WO 2006/012996 A1 on 9 Feb. 2006, which is entitled to the right of priority of German Patent Application No. DE 102004037366.3 filed on 30 Jul. 2004.

The invention relates to novel 1-cycloalkyl-5-iodotetrazoles, to processes for their preparation and to their use as biocides for protecting plants and industrial materials.

Some 5-iodotetrazoles and routes for their preparation are already known from the literature. A biological action is not mentioned in any of the prior-art examples. 1-Cycloalkyl-5-iodotetrazoles are not known in the literature.

5-Iodotetrazoles can also be obtained by reacting 1-substituted 5-tetrazolyllithium compounds at low temperatures with iodine (cf. R. Raap, Can. J. Chem. 1971, 49, 2139; Satoh, Yoshitaka; Tetrahedron Lett., 1995, 36, 1759; Satoh, Yoshitaka, Synlett 1998, 528).

A further process for preparing 1-alkyl-5-iodotetrazoles uses 1-alkyltetrazoles as starting materials which are treated with iodine in glacial acetic acid containing $KMnO_4$ and $H_2SO_4$ (cf. P. N. Gaponik, Khimiya Geterotsiklicheskikh Soedinenii 1988, 1699).

Novel 5-iodotetrazoles which are substituted by cycloalkyl in the 1-position have now been found, which are highly suitable as microbicides for protecting plants and industrial materials.

Accordingly, the present invention provides novel compounds of the formula (I)

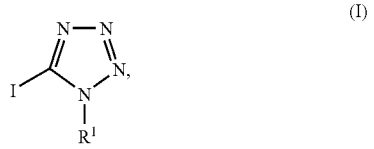

in which $R^1$ represents cycloalkyl.

Preference is given to compounds of the general formula (I), in which $R^1$ represents optionally bridged $C_3$-$C_8$-cycloalkyl which is unsubstituted or mono- or polysubstituted by identical or different substituents,
where the substituents for the cycloalkyl radicals which are mono- or polysubstituted by identical or different substituents are selected from the group consisting of halogen; nitro; cyano; hydroxyl; unsubstituted $C_1$-$C_8$-alkyl; $C_1$-$C_8$-alkyl which is mono- to nonasubstituted by identical or different halogen substituents; $C_2$-$C_8$-alkynyl; unsubstituted $C_1$-$C_8$-alkoxy; $C_1$-$C_8$-alkoxy which is mono- to nonasubstituted by identical or different halogen substituents; unsubstituted $C_1$-$C_8$-alkylthio; $C_1$-$C_8$-alkylthio which is mono- to nonasubstituted by identical or different halogen substituents; $C_3$-$C_8$-cycloalkyl; amino; monoalkylamino having straight-chain or branched $C_1$-$C_8$-alkyl radicals; dialkylamino having identical or different straight-chain or branched $C_1$-$C_8$-alkyl radicals; $C_1$-$C_8$-acyl; $C_1$-$C_8$-acyloxy; $C_1$-$C_8$-alkoxycarbonyl; carboxyl; unsubstituted phenyl; phenyl which is mono- to pentasubstituted by identical or different substituents from the group consisting of halogen, nitro, cyano, alkyl, haloalkyl, alkoxy, haloalkoxy, alkylthio, haloalkylthio, acyl, acyloxy, alkoxycarbonyl, carboxyl, amino, monoalkylamino and dialkylamino.

Particular preference is given to compounds of the general formula (I) in which $R^1$ represents optionally bridged $C_3$-$C_8$-cycloalkyl which is unsubstituted or mono- to hexasubstituted by identical or different substituents,
where the substituents for the $C_3$-$C_8$-cycloalkyl radicals which are mono- to hexasubstituted by identical or different substituents are selected from the group consisting of fluorine; chlorine; bromine; iodine; nitro; cyano; hydroxyl; unsubstituted $C_1$-$C_6$-alkyl; $C_1$-$C_6$-alkyl which is mono- to hexasubstituted by identical or different substituents from the group consisting of fluorine, chlorine and bromine; $C_2$-$C_8$-alkynyl; $C_1$-$C_6$-alkoxy; $C_1$-$C_6$-alkoxy which is mono- to hexasubstituted by identical or different substituents from the group consisting of fluorine, chlorine and bromine; unsubstituted $C_1$-$C_6$-alkylthio; $C_1$-$C_6$-alkylthio which is mono- to hexasubstituted by identical or different substituents from the group consisting of fluorine, chlorine and bromine; $C_3$-$C_6$-cycloalkyl; amino; monoalkylamino having straight-chain or branched $C_1$-$C_6$-alkyl radicals; dialkylamino having identical or different straight-chain or branched $C_1$-$C_6$-alkyl radicals; $C_1$-$C_6$-acyl; $C_1$-$C_6$-acyloxy; $C_1$-$C_6$-alkoxycarbonyl; carboxyl; unsubstituted phenyl; phenyl which is mono- to tetrasubstituted by identical or different substituents from the group consisting of fluorine, chlorine, bromine, iodine, nitro, cyano, hydroxyl, $C_1$-$C_4$-alkyl, $C_1$-$C_4$-haloalkyl which is mono- to pentasubstituted by identical or different substituents from the group consisting of fluorine, chlorine and bromine, $C_1$-$C_4$-alkoxy, $C_1$-$C_4$-haloalkoxy which is mono- to pentasubstituted by identical or different substituents from the group consisting of fluorine, chlorine and bromine, $C_1$-$C_4$-alkylthio, $C_1$-$C_4$-haloalkylthio which is mono- to pentasubstituted by identical or different substituents from the group consisting of fluorine, chlorine and bromine, $C_1$-$C_6$-acyl, $C_1$-$C_6$-acyloxy, $C_1$-$C_6$-alkoxycarbonyl, carboxyl, amino, monoalkylamino having straight-chain or branched $C_1$-$C_4$-alkyl radicals, dialkylamino having identical or different straight-chain or branched $C_1$-$C_4$-alkyl radicals.

Very particular preference is given to compounds of the formula (I) in which $R^1$ represents optionally bridged cyclopropyl, cyclobutyl, cyclopentyl, cyclohexyl, cycloheptyl, cyclooctyl, adamantyl which is unsubstituted or mono- to tetrasubstituted by identical or different substituents,
where the cycloalkyl radicals mentioned are in each case optionally mono- to tetrasubstituted by identical or different substituents from the group consisting of fluorine, chlorine, bromine, iodine, nitro, cyano, hydroxyl, methyl, ethyl, n-propyl, isopropyl, n-butyl, isobutyl, sec-butyl, tert-butyl, pentyl, hexyl, trifluoromethyl, ethynyl, propynyl, butynyl, pentynyl, hexynyl, methoxy, ethoxy, n-propoxy, isopropoxy, n-butoxy, isobutoxy, sec-butoxy, tert-butoxy, pentoxy, trifluoromethoxy, methylthio, ethylthio, n-propylthio, isopropylthio, trifluoromethylthio, cyclopropyl, cyclobutyl, cyclopentyl, cyclohexyl, amino, methylamino, ethylamino, n-propylamino, isopropylamino, dimethylamino, diethylamino, methylethylamino, di-n-propylamino, diisopropylamino, acetyl, acetyloxy, methoxycarbonyl, carboxyl, unsubstituted phenyl, phenyl which is mono- to trisubstituted by fluorine, chlorine, bromine, iodine, nitro, cyano, hydroxyl, methyl, ethyl, n-propyl, isopropyl, n-butyl, isobutyl, sec-butyl, tert-butyl, trifluoromethyl, methoxy, ethoxy, n-propoxy, isopropoxy, n-butoxy, isobutoxy, sec-butoxy, tert-butoxy, trifluoromethoxy, methylthio, ethylthio, n-propylthio, isopropylthio, trifluoromethylthio, formyl, acetyl, acetyloxy, methoxycarbonyl, ethoxycarbonyl, carboxyl, amino, methylamino, ethylamino, n-propylamino, isopropylamino, dimethylamino, diethylamino, methylethylamino, di-n-propylamino, diisopropylamino.

The radicals given in the respective definitions and preferred, particularly preferred and very particularly preferred definitions may, independently of the particular given combination, also be replaced by any radical definitions of other combinations. Moreover, radical definitions from a preferred range may not apply.

Depending on the substitution, the compounds of the formula (I) may also be chiral. The invention also comprises any stereoisomers that may occur, and any mixtures thereof. In the context of the invention, the terms stereoisomerically enriched (enantiomerically enriched or diastereomerically enriched) refer to stereoisomerically pure (enantiomerically pure or diastereomerically pure) compounds or mixtures of stereoisomers (enantiomers or diastereomers) in which one stereoisomer (enantiomer or diastereomer) is present in a proportion higher than that of another stereoisomer/the other stereoisomer. By way of example and by way of preference, stereoisomerically enriched means a stereoisomer content of from 50% to 100% by weight, particularly preferably from 70% to 100% by weight and very particularly preferably from 90 to 100% by weight, based on the sum of the respective stereoisomers.

Enrichment and separation of the racemates and/or diastereomer mixtures may be by physical processes utilizing optionally optically active carrier materials having a preferred affinity to one of the enantiomers or diastereomers. Inclusion compounds may be mentioned by way of example. It is furthermore possible to carry out the enrichment and separation of the racemates and/or diastereomer mixtures by chromatographic methods on optionally optically active absorbents, for example cyclodextrins, starch or modified silica gels. It is furthermore possible to carry out the enrichment and separation of the racemates by addition of an optically active auxiliary.

Optionally bridged $C_3$-$C_8$-cycloalkyl in the definition of $R^1$ is to be understood as meaning that at least 2 carbon atoms of the $C_3$-$C_8$-cycloalkyl radical are components of at least one further attached ring.

Preferably, optionally bridged $C_3$-$C_8$-cycloalkyl in the definition of $R^1$ is to be understood as meaning that optionally at least 2 carbon atoms of the $C_3$-$C_8$-cycloalkyl radical are components of up to three further attached rings, the attached rings, if appropriate, each having a size of 3 to 10 carbon atoms.

Particularly preferably, optionally bridged $C_3$-$C_8$-cycloalkyl is to be understood as meaning that optionally at least 2 carbon atoms of the $C_3$-$C_8$-cycloalkyl radical are components of up to three further attached rings, the attached rings, if appropriate, each having a size of 3 to 6 carbon atoms.

The novel compounds of the general formula (I) can be prepared by treating tetrazoles of the general formula (II),

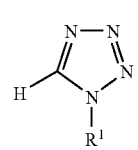

(II)

in which $R^1$ has the general or preferred meaning given above, with iodine, if appropriate in the presence of a base or a diluent.

In general, the temperature in the processes may be varied within a wide range. As rule, the reaction is carried out between 50° C. and −100° C., preferably at from 30° C. to −90° C.; with very particular preference, the operations are carried out in a range from 10° C. to −80° C.

Suitable bases are, in principle, all customary bases. Strong bases, such as alkali metal amides and alkali metal alkyl compounds, have been found to be particularly advantageous. The following may be mentioned as being very particularly preferred: lithium diisopropylamide, methyllithium, ethyllithium, propyllithium, n-butyllithium, tert-butyllithium, sodium hexamethyldisilazide, lithium hexamethyldisilazide.

Suitable for use as diluents are all solvents which do not react with iodine or the base which is added, if appropriate. These solvents preferably include hydrocarbons, such as toluene, xylene or hexane, chlorinated hydrocarbons, such as chlorobenzene, methylene chloride or chloroform, ethers, such as tetrahydrofuran, diethyl ether, methyl tert-butyl ether and dioxane, nitriles, such as acetonitrile, and also DMSO, DMF and NMP.

The compounds of the general formula (I) can furthermore be obtained by reacting tetrazoles of the general formula (II) in which $R^1$ is as defined above with iodine, if appropriate in the presence of an acid and, if appropriate, in the presence of an oxidizing agent.

This reaction is generally carried out between 0° C. and 150° C., preferably between 20° C. and 130° C. and particularly preferably between 80° C. and 110° C.

Suitable for use as acids are all customary acids. Preference is given to using acetic acid or sulphuric acid.

Suitable for use as oxidizing agents are all customary oxidizing agents; preference is given to using $KMnO_4$, $HNO_3$, $H_2O_2$ or peracetic acid; very particular preference is given to using $KMnO_4$.

The preparation processes afford the compounds of the general formula (I) as a racemate, if the compounds of the general formula (II) have a stereogenic center, or, if the compounds of the general formula (II) have more than one stereogenic center, as a mixture of diastereomers. The racemates and diastereomer mixtures may be used as such or be enriched by processes known to the person skilled in the art and converted into the enantiomers or diastereomerically pure compounds.

Except for the compounds having the CAS numbers below, the compounds of the general formula (II) are likewise novel and also form part of the subject-matter of the present invention:

[280131-31-9]: 5H-cyclopenta[c]pyridin-1-amine, 6,7-dihyrdo-6-(1H-tetrazol-1-yl)-;

[280131-30-8]: 5H-cyclopenta[c]pyridin-1-amine, 6,7-dihydro-5-(1H-tetrazol-1-yl)-;

[280131-27-3]: 5H-cyclopenta[c]pyridin-1-amine, 6,7-dihydro-7-(1H-tetrazol-1-yl)-;
[207729-97-3]: cyclopentanamine, 2-(4-fluorophenyl)-3-(1H-tetrazol-1-yl)-, (1R,2S,3R);
[190270-66-7]: cyclopentanamine, 2-(4-fluorophenyl)-3-(1H-tetrazol-1-yl)-, (1α,2α,3β)-;
[190270-65-6]: 1H-tetrazole, 1-[3-azido-2-(4-fluorophenyl)cyclopentyl]-, (1α,2β,3β)-;
[190270-64-5]: cyclopentanol, 2-(4-fluorophenyl)-3-(1H-tetrazol-1-yl)-, (1R,2S,3S);
[190270-63-4]: 1H-tetrazole, 1-[(1R,2R,3S)-2-(4-fluorophenyl)-3-(phenylmethoxy)cyclopentyl]-;
[103312-35-2]: 1H-tetrazole, 1-(6-chloro-2,3-dihydro-5-methyl-1H-inden-1-yl)-;
[103294-76-4]: 1H-tetrazole, 1-(5,6-dichloro-2,3-dihydro-1H-inden-1-yl)-;
[720721-24-4]: carbamic acid, [(1R,2S,5S)-2-[[[(5-chloro-2-pyridinyl)amino]oxoacetyl]amino]-5-(1H-tetrazol-1-yl)cyclohexyl]-, 1,1-dimethylethyl ester;
[720721-23-3]: carbamic acid, [(1S,2R,4S)-2-[[(1,1-dimethylethoxy)carbonyl]amino]-4-(1H-tetrazol-1-yl)cyclohexyl]-, phenylmethyl ester;
[160698-27-1]: 1H-tetrazole, 1-(1,2,3,4-tetrahydro-1-naphthalenyl)-;
[160698-25-9]: 1H-tetrazole, 1-(1-ethyl-1,2,3,4-tetrahydro-1-naphthalenyl)-;
[5098742-3]: 1H-tetrazole, 1-tricyclo[3.3.1.13,7]dec-2-yl-; (adamantyl)
[50987-38-7]: 1H-tetrazole, 1-tricyclo[3.3.1.13,7]dec-1-yl-; (adamantyl)
[24281-91-2]: 1H-tetrazole, 1-(5α-cholestan-3β-yl)-;
[24281-90-1]: 1H-tetrazole, 1-(5α-cholestan-3α-yl)-;
[24281-82-1]: 1H-tetrazole, 1-(5α-cholestan-6β-yl)-;
[24211-56-1]: 1H-tetrazole, 1-(5α-cholestan-6α-yl)-;
[18102-76-6]: 1H-tetrazole, 1-cyclohexyl-.

The compounds of the general formula (II) can be prepared by the person skilled in the art using generally known methods, for example by reacting a primary amine with triethyl orthoformate and sodium azide in acetic acid (cf., for example, Science of Synthesis, Volume 13, page 864).

The compounds of the formula (I) in which $R^1$ has the general and preferred meanings indicated above exhibit pronounced activity against microorganisms relevant in crop protection and the protection of materials, and they can be used as microbicides for protecting plants and industrial materials.

Accordingly, the present invention also provides the use of the compounds of the formula (I) for protecting plants and industrial materials against attack and/or destruction by microorganisms.

The compounds of the formula (I) have strong microbicidal action and can be used for controlling unwanted microorganisms, such as, for example, fungi, bacteria and algae. The compounds of the formula (I) are preferably used for controlling unwanted microorganisms in the protection of materials.

In the protection of materials, the compounds according to the invention can be used for protecting industrial materials against attack and destruction by unwanted microorganisms.

In the present context, industrial materials are to be understood as meaning non-living materials which have been prepared for use in industry. Industrial materials are, for example, glues, sizes, paper and cardboard, textiles, leather, wood, timber products, wood composites, paints and plastics, cooling lubricants and other materials which can be attacked or destroyed by microorganisms. Parts of production plants, for example cooling-water circuits, which may be impaired by the multiplication of microorganisms may also be mentioned as industrial materials in the context of the present invention. Industrial materials which are preferably to be protected are glues, sizes, paper and cardboard, leather, wood, timber products, wood composites, paints, plastics, cooling lubricants and heat transfer liquids.

The compounds of the formula (I) according to the invention are particularly suitable for protecting wood, timber products, wood composites, plastics, cooling lubricants, aqueous and/or solvent-containing organic or inorganic dispersions and coating systems, such as paints, varnishes or plasters against attack by microorganisms.

Examples of microorganisms which are capable of brining about degradation of, or change in, the industrial materials and which may be mentioned are bacteria, fungi, yeast, algae and slime organisms. The active compounds of the formula (I) according to the invention preferably act against fungi, in particular moulds, wood-discolouring and wood-destroying fungi (Basidiomycetes) and also against slime organisms and bacteria.

Microorganisms of the following genera may be mentioned by way of example:

*Alternaria*, such as *Alternaria tenuis*,

*Aspergillus*, such as *Aspergillus niger*,

*Chaetomium*, such as *Chaetomium globosum*,

*Coniophora*, such as *Coniophora puetana*,

*Lentinus*, such as *Lentinus tigrinus*,

*Penicillium*, such as *Penicillium glaucum*,

*Polyporus*, such as *Polyporus versicolor*,

*Aureobasidium*, such as *Aureobasidium pullulans*,

*Sclerophoma*, such as *Sclerophoma pityophila*,

*Trichoderma*, such as *Trichoderma viride*,

*Escherichia*, such as *Escherichia coli*,

*Pseudomonas*, such as *Pseudomonas aeruginosa*,

*Staphylococcus*, such as *Staphylococcus aureus*.

The compounds (I) according to the invention can be used individually or in any mixture with one another for protecting industrial materials.

Depending on their respective physical and/or chemical properties, the active compounds or mixtures thereof can furthermore be converted into customary formulations, such as solutions, emulsions, suspensions, powders, foams, pastes, granules, aerosols and very fine capsules in polymeric substances.

These formulations and compositions are prepared in a known manner, for example by mixing the active compounds with extenders, that is, liquid solvents, liquefied gases under pressure, and/or solid carriers, if appropriate with the use of surfactants, that is emulsifiers and/or dispersants and/or foam-formers. If the extender used is water, it is also possible to use for example organic solvents as auxiliary solvents. Essentially, suitable liquid solvents are: aromatics, such as xylene, toluene or alkylnaphthalenes, chlorinated aromatics or chlorinated aliphatic hydrocarbons, such as chlorobenzenes, chloroethylene or methylene chloride, aliphatic hydrocarbons, such as cyclohexane or paraffins, for example mineral oil fractions, alcohols, such as butanol or glycol and their ethers and esters, ketones, such as acetone, methyl ethyl ketone, methyl isobutyl ketone or cyclohexanone, strongly polar solvents, such as dimethyl formamide and dimethyl sulphoxide, and water. By liquefied gaseous extenders or carriers are meant liquids which are gaseous at ambient temperature and under atmospheric pressure, for example aerosol propellants, such as halogenated hydrocarbons and butane, propane, nitrogen and carbon dioxide. Suitable solid carriers are: for example ground natural minerals, such as kaolins, clays, talc, chalk, quartz, attapulgite, montmorillonite or diatomaceous earth, and ground synthetic minerals, such as finely divided silica, alumina and silicates. Suitable solid carriers for granules are: for example crushed and fractionated natural rocks such as calcite, marble, pumice, sepiolite and dolomite, and synthetic granules of organic and inorganic meals, and granules of organic material such as sawdust, coconut shells, maize cobs and tobacco stalks. Suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Other possible additives are mineral and vegetable oils.

It is possible to use colourants such as inorganic pigments, for example iron oxide, titanium oxide and Prussian blue, and organic dyestuffs, such as alizarin dyestuffs, azo dyestuffs and metal phthalocyanin dyestuffs, and trace nutrients such as salts of iron, manganese, boron, copper, cobalt, molybdenum and zinc.

The formulations generally comprise between 0.1 and 95 percent by weight of active compound, preferably between 2 and 75 percent by weight.

The present invention thus further relates to microbicidal compositions based on the compounds of the formula (I) according to the invention and comprising at least one solvent or diluent and also, if appropriate, processing auxiliaries and, if appropriate, further antimicrobially active compounds. In this case, the active compounds may be present herein either in dissolved form or as suspensions or emulsions. The solvents or diluents are either water or all customary organic solvents.

The compositions according to the invention may be prepared by mixing at least one compound of the formula (I) with at least one solvent or diluent and, where appropriate, with auxiliaries and additives and, where appropriate, other antimicrobially active compounds.

The efficacy and the activity spectrum of the active compounds of the formula (I) and of the compositions preparable therefrom, of precursors or of formulations in general can be increased by adding, if appropriate, further antimicrobial compounds, fungicides, bactericides, herbicides, insecticides or other active compounds, so as to widen the spectrum of activity or to obtain particular effects. These mixtures may have a wider activity spectrum than the compounds according to the invention.

In many cases, synergistic effects are obtained, i.e. the activity of the mixture is greater than the activity of the individual components. The following co-components are found to be particularly favorable:

triazoles such as:

azaconazole, azocyclotin, bitertanol, bromuconazole, cyproconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazole, penconazole, propioconazole, prothioconazole, simeoconazole, (±)-cis-1-(4-chlorophenyl)-2-(1H-1,2,4-triazol-1-yl)cycloheptanol, 2-(1-tert-butyl)-1-(2-chlorophenyl)-3-(1,2,4-triazol-1-yl) propan-2-ol, tebuconazole, tetraconazole, triadimefon, triadimenol, triapenthenol, triflumizole, triticonazole, uniconazole and their metal salts and acid adducts;

imidazoles such as:

clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chlorophenoxy)-3,3-dimethylbutan-2-one, and their metal salts and acid adducts;

pyridines and pyrimidines such as:

ancymidol, buthiobate, fenarimol, mepanipyrin, nuarimol, pyvoxyfur, triamirol;

succinate dehydrogenase inhibitors such as:

benodanil, carboxim, carboxim sulphoxide, cyclafluramid, fenfuram, flutanil, furcarbanil, furmecyclox, mebenil, mepronil, methfuroxam, metsulphovax, nicobifen, pyrocarbolid, oxycarboxin, Shirlan, Seedvax;

naphthalene derivatives such as:

terbinafine, naftifine, butenafine, 3-chloro-7-(2-aza-2,7,7-trimethyloct-3-en-5-yne);

sulphenamides such as:

dichlofluanid, tolylfluanid, folpet, fluorofolpet, captan, captofol;

benzimidazoles such as:

carbendazim, benomyl, fuberidazole, thiabendazole or their salts;

morpholine derivatives such as:

aldimorph, dimethomorph, dodemorph, falimorph, fenpropidin, fenpropimorph, tridemorph, trimorphamid and their arylsulphonate salts such as, for example, p-toluenesulphonic acid and p-dodecylphenylsulphonic acid;

benzothiazoles such as:

2-mercaptobenzothiazole;

benzothiophene dioxides such as:

N-cyclohexyl-benzo[b]thiophenecarboxamide S,S-dioxide;

benzamides such as:

2,6-dichloro-N-(4-trifluoromethylbenzyl)benzamide, tecloftalam;

boron compounds such as:

boric acid, boric ester, borax;

formaldehyde and formaldehyde-releasing compounds such as:

benzyl alcohol mono(poly)hemiformal, 1,3-bis(hydroxymethyl)-5,5-dimethylimidazolidine-2,4-dione (DMDMH), bisoxazolidine, n-butanol hemiformal, cis-1-(3-chloroallyl)-3,5,7-triaza-1-azoniaadamantane chloride, 1-[1,3-bis(hydroxymethyl-2,5-dioxoimidazolidin-4-yl]-1,3-bis-(hydroxymethyl)urea, dazomet, dimethylolurea, 4,4-dimethyloxazolidine, ethylene glycol hemiformal, 7-ethylbicyclooxazolidine, hexahydro-S-triazine, hexamethylenetetramine, N-hydroxymethyl-N'-methylthiourea, methylenebismorpholine, sodium N-(hydroxymethyl)glycinate, N-methylolchloroacetamide, oxazolidine, paraformaldehyde, taurolin, tetrahydro-1,3-oxazine, N-(2-hydroxypropyl) aminemethanol, tetramethylolacetylenediurea (TMAD);

isothiazolinones such as:

N-methylisothiazolin-3-one, 5-chloro-N-methylisothiazolin-3-one, 4,5-dichloro-N-octyliso-thiazolin-3-one, 5-chloro-N-octylisothiazolinone, N-octylisothiazolin-3-one, 4,5-trimethyleneiso-thiazolinone, 4,5-benzoisothiazolinone;

aldehydes such as:

cinnamaldehyde, formaldehyde, glutardialdehyde, β-bromocinnamaldehyde, o-phthaldialdehyde;

thiocyanates such as:

thiocyanatomethylthiobenzothiazole, methylenebisthiocyanate;

quaternary ammonium compounds and guanidines such as:

benzalkonium chloride, benzyldimethyltetradecylammonium chloride, benzyldimethyl-dodecylammonium chloride, dichlorobenzyldimethylallylammonium chloride, didecyldimethyl-ammonium chloride, dioctyldimethylammonium chloride, N-hexadecyltrimethylammonium chloride, 1-hexadecylpyridinium chloride, iminoctadine tris(albesilate);

iodine derivatives such as:

diiodomethyl p-tolyl sulphone, 3-iodo-2-propynyl alcohol, 4-chlorophenyl-3-iodopropargylformal, 3-bromo-2,3-diiodo-2-propenyl ethylcarbamate, 2,3,3-triiodoallyl alcohol, 3-bromo-2,3-diiodo-2-propenyl alcohol, 3-iodo-2-propynyl n-butylcarbamate, 3-iodo-2-propynyl n-hexylcarbamate, 3-iodo-2-propynyl cyclohexylcarbamate, 3-iodo-2-propynyl phenylcarbamate;

phenols such as:

tribromophenol, tetrachlorophenol, 3-methyl-4-chlorophenol, 3,5-dimethyl-4-chlorophenol, dichlorophene, 2-benzyl-4-chlorophenol, triclosan, diclosan, hexachlorophene, methyl p-hydroxybenzoate, ethyl p-hydroxybenzoate, propyl p-hydroxybenzoate, butyl p-hydroxybenzoate, octyl p-hydroxybenzoate, o-phenylphenol, m-phenylphenol, p-phenylphenol 4-(2-tert-butyl-4-methylphenoxy)phenol, 4-(2-isopropyl-4-methylphenoxy)phenol, 4-(2,4-dimethylphenoxy)phenol and their alkali metal salts and alkaline earth metal salts;

microbicides with an activated halogen group such as:

bronopol, bronidox, 2-bromo-2-nitro-1,3-propanediol, 2-bromo-4'-hydroxyacetophenone,1-bromo-3-chloro-4,4,5,5-tetramethyl-2-imidazolidinone, β-bromo-β-nitrostyrene, chloracetamide, chloramine T, 1,3-dibromo-4,4,5,5-tetramethyl-2-imidazolidinone, dichloramine T, 3,4-dichloro-(3H)-1,2-dithiol-3-one, 2,2-dibromo-3-nitrilepropionamide, 1,2-dibromo-2,4-dicyanobutane, halane, halazone, mucochloric acid, phenyl (2-chlorocyanovinyl)sulphone, phenyl (1,2-dichloro-2-cyanovinyl)sulphone, trichloroisocyanuric acid;

pyridines such as:

1-hydroxy-2-pyridinethione (and their Cu, Na, Fe, Mn, Zn salts), tetrachloro-4-methyl-sulphonylpyridine, pyrimethanol, mepanipyrim, dipyrithion, 1-hydroxy-4-methyl-6-(2,4,4-trimethylpentyl)-2(1H)-pyridine;

methoxyacrylates or similar such as:

azoxystrobin, dimoxystrobin, fluoxastrobin, kresoxim-methyl, metominostrobin, orysastrobin, picoxystrobin, pyraclostrobin, trifloxystrobin, 2,4-dihydro-5-methoxy-2-methyl-4-[2-[[[[1-[3-(trifluoromethyl)phenyl]ethylidene]amino]oxy]methyl]phenyl]-3H-1,2,4-triazol-3-one (CAS-No. 185336-79-2);

metal soaps such as:

salts of the metals tin, copper and zinc with higher fatty acids, resin acids, naphthenoic acids and phosphoric acid, and as, for example, tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;

metal salts such as:

salts of the metals tin, copper, zinc, and also chromates and dichromates, such as, for example, copper hydroxycarbonate, sodium dichromate, potassium dichromate, potassium chromate, copper sulphate, copper chloride, copper borate, zinc fluorosilicate, copper fluorosilicate;

oxides such as:

oxides of the metals tin, copper and zinc, such as, for example, tributyltin oxide, $Cu_2O$, CuO, ZnO;

oxidizing agents such as:

hydrogen peroxide, peracetic acid, potassium persulphate;

dithiocarbamates such as:

cufraneb, ferban, potassium N-hydroxymethyl-N'-methyldithiobarbamate, sodium dimethyldithiocarbamate, potassium, dimethyldithiocarbamate, macozeb, maneb, metam, metiram, thiram, zineb, ziram;

nitriles such as:

2,4,5,6-tetrachloroisophthalonitrile, disodium cyanodithioimidocarbamate;

quinolines such as:

8-hydroxyquinoline and their copper salts;

other fungicides and bactericides such as:

bethozaxin, 5-hydroxy-2(5H)-furanone, 4,5-benzodithiazolinone, 4,5-trimethylenedithiazolinone, N-(2-p-chlorobenzoylethyl)hexaminium chloride, 2-oxo-2-(4-hydroxyphenyl) acetohydroxy-cinnamoyl chloride, tris-N-(cyclohexyldiazeniumdioxy)-aluminum, N-(cyclohexyldiazenium-dioxy)-tributyltin or its potassium salts, bis-N-(cyclohexyldiazeniumdioxy)-copper; iprovalicarb, fenhexamide, spiroxamine, carpropamid, diflumetorin, quinoxyfen, famoxadone, polyoxorim, acibenzolar S-methyl, furametpyr, thifluzamide, methalaxy-M, benthiavalicarb, metrafenon, cyflufenamid, tiadinil, tea tree oil, phenoxyethanol, Ag, Zn or Cu-containing zeolites alone or incorporated into polymeric materials.

Very especially preferred are mixtures with azaconazole, bromuconazole, cyproconazole, dichlobutrazol, diniconazole, diuron, hexaconazole, metaconazole, penconazole, propiconazole, tebuconazole, dichlofluanid, tolylfluanid, fluorfolpet, methfuroxam, carboxin, benzo[b]

thiophene S,S-dioxide cyclohexylcarboxamide, fenpiclonil, 4-(2,2-difluoro-1,3-benzodioxol-4-yl)-1H-pyrrole-3-carbonitrile, butenafine, imazalil, N-methyl-isothiazolin-3-one, 5-chloro-N-methylisothiazolin-3-one, N-octylisothiazolin-3-one, dichloro-N-octylisothiazolinone, mercaptobenthiazole, thiocyanatomethylthiobenzothiazole, thiabendazole, benzoisothiazolinone, N-(2-hydroxypropyl)aminomethanol, benzyl alcohol (hemi)formal, N-methylolchloroacetamide, N-(2-hydroxypropyl)aminemethanol, glutaraldehyde, omadine, Zn-omadine, dimethyl dicarbonate, 2-bromo-2-nitro-1, 3-propanediol, 3-iodo-2-propynyl n-butylcarbamate, bethoxazin, o-phthaldialdehyde, 2,2-dibromo-3-nitrilepropionamide, 1,2-dibromo-2,4-dicyanobutane, 1,3-bis(hydroxymethyl)-5,5-dimethylimidazolidine-2,4-dione (DMDMH), tetramethylolacetylenediurea (TMAD), ethyleneglycolhemiformal, p-hydroxybenzoic acid, carbendazim, chlorophen, 3-methyl-4-chlorophenol, o-phenylphenol.

Apart from with the abovementioned fungicides and bactericides, mixtures with a good efficacy are, moreover, also prepared with other active compounds:

insecticides/acaricides/nematicides:

abamectin, acephate, acetamiprid, acetoprole, acrinathrin, alanycarb, aldicarb, aldoxycarb, aldrin, allethrin, alpha-cypermethrin amidoflumet, amitraz, avermectin, azadirachtin, azinphos A, azinphos M, azocyclotin,

*Bacillus thuringiensis*, barthrin, 4-bromo-2(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bistrilfluoron, bromophos A, bromophos M, bufencarb, buprofezin, butathiophos, butocarboxim, butoxycarboxim, cadusafos, carbaryl, carbofuran, carbophenothion, carbosulphan, cartap, quinomethionate, cloethocarb, 4-chloro-2-(2-chloro-2-methylpropyl)-5-[(6-iodo-3-pyridinyl)methoxy]-3 (2H)-pyridazinone (CAS-RN: 120955-77-3), chlordane, chlorethoxyfos, chlorfenapyr, chlorfenvinphos, chlorfluazuron, chlormephos, N-[(6-chloro-3-pyridinyl)methyl]-N'-cyano-N-methylethane-imidamide, chlorpicrin, chlorpyrifos A, chlorpyrifos M, cis-resmethrin, clocythrin, clothiazoben cypophenothrin clofentezin, coumaphos, cyanophos, cycloprothrin, cyfluthrin, cyhalothrin, cyhexatin, cypermethrin, cyromazin, decamethrin, deltamethrin, demeton M, demeton S, demeton-S-methyl, diafenthiuron, dialiphos, diazinon, 1,2-dibenzoyl-1(1,1-dimethyl)hydrazine, DNOC, dichlofenthion, dichlorvos, dicliphos, dicrotophos, difethialone, diflubenzuron, dimethoate, 3,5-dimethylphenyl methylcarbamate, dimethyl(phenyl)silylmethyl-3-phenoxybenzyl ether, dimethyl (4-ethoxyphenyl)silylmethyl-3-phenoxybenzyl ether, dimethylvinphos, dioxathion, disulphoton, eflusilanate, emamectin, empenthrin, endosulphan, EPN, esfenvalerate, ethiofencarb, ethion, ethofenprox, etrimphos, etoxazole, etobenzanid, fenamiphos, fenazaquin, fenbutatin oxide, fenfluthrin, fenitrothion, fenobucarb, fenothiocarb, fenoxycarb, fenpropathrin, fenpyrad, fenpyroximate, fensulphothion, fenthion, fenvalerate, fipronil, flonicamid, fluacrypyrim, fluazuron, flucycloxuron, flucythrinate, flufenerim, flufenoxuron, flupyrazofos, flufenzine, flumethrin, flufenprox, fluvalinate, fonophos, formethanate, formothion, fosmethilan fosthiazate, fubfenprox, furathiocarb, halofenocid, HCH, (CAS RN: 58-89-9), heptenophos, hexaflumuron, hexythiazox, hydramethylnon, hydroprene, imidacloprid, imiprothrin, indoxycarb, iodfenfos, iprinomectin, iprobenfos, isazophos, isoamidophos, isofenphos, isoprocarb, isoprothiolane, isoxathion, ivermectin, kadedrin lambda-cyhalothrin, lufenuron, malathion, mecarbam, mervinphos, mesulphenphos, metaldehyde, methacrifos, methamidophos, methidathion, methiocarb, methomyl, metalcarb, milbemectin, monocrotophos, moxiectin, naled, NI 125, nicotine, nitenpyram, noviflumuron, omethoate, oxamyl, oxydemethon M, oxydeprofos, parathion A, parathion M, penfluron, permethrin, 2-(4-phenoxyphenoxy)ethyl ethylcarbamate, phenthoate, phorate, phosalon, phosmet, phosphamidon, phoxim, pirimicarb, pirimiphos M, pirimiphos A, prallethrin, profenophos, promecarb, propaphos, propoxur, prothiophos, prothoate, pymetrozin, pyrachlophos, pyridaphenthion, pyresmethrin, pyrethrum, pyridaben, pyridalyl, pyrimidifen, pyriproxifen, pyrithiobac-sodium, quinalphos, resmethrin, rotenone, salithion, sebufos, silafluofen, spinosad, spirodiclofen, spiromesifen, sulphotep, sulprofos, tau-fluvalinate, taroils, tebufenozide, tebufenpyrad, tebupirimphos, teflubenzuron, tefluthrin, temephos, terbam, terbufos, tetrachlorvinphos, tetramethrin, tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamate, triazuron trichlorfon, triflumuron, trimethacarb, vamidothion, xylylcarb, zetamethrin;

molluscicides:

fentin acetate, metaldehyde, methiocarb, niclosamide;

herbicides and algaecides:

acetochlor, acifluorfen, aelonifen, acrolein, alachlor, alloxydim, ametryn, amidosulphuron, amitrole, ammonium sulphamate, anilofos, asulam, atrazine, azafenidin, aziptrotryne, azimsulphuron, benazolin, benfluralin, benfuresate, bensulphuron, bensulphide, bentazone, benzofencap, benzthiazuron, bifenox, bispyribac, bispyribac-sodium, borax, bromacil, bromobutide, bromofenoxim, bromoxynil, butachlor, butamifos, butralin, butylate, bialaphos, benzoyl-prop, bromobutide, butroxydim, carbetamide, carfentrazone-ethyl, carfenstrole, chlomethoxyfen, chloramben, chlorbromuron, chlorflurenol, chloridazon, chlorimuron, chlornitrofen, chloroacetic acid, chloransulam-methyl, cinidon-ethyl, chlorotoluron, chloroxuron, chlorpropham, chlorsulphuron, chlorthal, chlorthiamid, cinmethylin, cinofulsuron, clefoxydim, clethodim, clomazone, chlomeprop, clopyralid, cyanamide, cyanazine, cycloate, cycloxydim, chloroxynil, clodinafop-propargyl, cumyluron, clometoxyfen, cyhalofop, cyhalofop-butyl, clopyrasuluron, cyclosulphamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomet, 2,4-DB, desmedipham, desmetryn, dicamba, dichlobenil, dimethamid, dithiopyr, dimethametryn, eglinazine, endothal, EPTC, esprocarb, ethalfluralin, ethidimuron, ethofumesate, ethobenzanid, ethoxyfen, ethametsulphuron, ethoxysulphuron, fenoxaprop, fenoxaprop-P, fenuron, flamprop, flamprop-M, flazasulphuron, fluazifop, fluazifop-P, fuenachlor, fluchloralin, flufenacet, flumeturon, fluorocglycofen, fluoronitrofen, flupropanate, flurenol, fluridone, fluorochloridone, fluoroxypyr, fomesafen, fosamine, fosametine, flamprop-isopropyl, flamprop-isopropyl-L, flufenpyr flumiclorac-pentyl, flumipropyn, flumioxzim, flurtamone, flumioxzim, flupyrsulphuron-methyl, fluthiacet-methyl, glyphosate, glufosinate-ammonium haloxyfop, hexazinone, imazamethabenz, isoproturon, isoxaben, isoxapyrifop, imazapyr, imazaquin, imazethapyr, ioxynil, isopropalin, imazosulphuron, imazomox, isoxaflutole, imazapic, ketospiradox, lactofen, lenacil, linuron, MCPA, MCPA-hydrazide, MCPA-thioethyl, MCPB, mecoprop, mecoprop-P, mefenacet, mefluidide, mesosulphuron metam, metamifop, metamitron, metazachlor, methabenzthiazuron, methazole, methoroptryne, methyldymron, methyl isothiocyanate, metobromuron, metoxuron, metribuzin, metsulphuron, molinate, manolide, monolinuron, MSMA, metolachlor, metosulam, metobenzuron, naproanilide, napropamide, naptalam, neburon, nicosulphuron, norflurazon, sodium chloride, oxadiazon, oxyfluorfen, oxysulphuron, orbencarb, oryzalin, oxadiargyl, propyzamide, prosulphocarb, pyrazolate, pyrazolsulphuron, pyrazoxyfen, pyribenzoxim, pyributicarb, pyridate, paraquat, pebulate, pendimethalin, pentachlorophenol, pentoxazone, pentanochlor, petroleum oils, phenmedipham, picloram, piperophos, pretilachlor, primisulphuron, prodiamine, profoxydim, prometryn, propachlor, propanil, propaquizafob, propazine, propham, propisochlor, pyriminobac-methyl, pelargonic acid, pyrithiobac, pyraflufen-ethyl, quinmerac, quinocloamine, quizalofop, quizalofop-P, quinchlorac, rimsulphuron sethoxydim, sifuron, simazine, simetryn, sulphosulphuron, sulphometuron, sulphentrazone, sulcotrione, sulphosate, tar oils, TCA, TCA-sodium, tebutam, tebuthiuron, terbacil, terbumeton, terbuthylazine, terbutryn, thiazafluoron, thifensulphuron, thiobencarb, thiocarbazil, tralkoxydim, triallate, triasulphuron, tribenuron, tricloyr, tridiphane, trietazine, trifluralin, tycor, thdiazimin, thiazopyr, triflusulphuron, vernolate.

The weight ratios of the active compounds in these active compound combinations can be varied within relatively wide ranges.

Preferably, the active compound combinations comprise the active compound in an amount of from 0.1 to 99.9%, in particular from 1 to 75%, especially preferably from 5 to 50%, the remainder to 100% being one or more of the co-components mentioned above.

The microbicidal compositions or concentrates used for protecting the industrial materials comprise the active compound or the active compound combination in a concentration of 0.01 and 95 percent by weight, in particular from 0.1 to 60 percent by weight.

The use concentrations of the active compounds or active compound combinations to be used depend on the nature and the occurrence of the microorganisms to be controlled and on the composition of the material to be protected. The optimum rate of application can be determined by test series. In general, the use concentrations are in the range from 0.001 to 5 percent by weight, preferably from 0.05 to 2.5 percent by weight, based on the material to be protected.

With the active compounds or compositions according to the invention, it is possible to replace, in an advantageous manner, the microbicidal compositions available to date by more effective compositions. They have good stability and, in an advantageous manner, a broad activity spectrum. The active compounds can be applied as such, in the form of their formulations or in the use forms prepared therefrom, such as ready-to-use solutions, emulsions, suspensions, wettable powders, pastes, soluble powders, dustable products and granules. Application is carried out in a customary manner, for example by watering, spraying, atomizing, broadcasting, dusting, foaming, spreading, etc.

The examples below are given to illustrate the present invention, without limiting it in any way. Wile the present invention has been described with reference to specific details and examples of particular embodiments thereof, it is not intended that such details and examples be regarded as limitations upon the scope of the invention except insofar as and to the extent that they are included in the accompanying claims.

EXAMPLE 1

1-Cyclopentyl-5-iodotetrazole

In an atmosphere of inert gas, 10.42 mmol of butyllithium (1.6M in hexane) was added dropwise to a solution, cooled to −75° C., of 8.68 mmol (1.20 g) of 1-cyclopentyltetrazole in 27 ml of anhydrous tetrahydrofuran such that the temperature of the reaction mixture did not exceed −70° C. The mixture was stirred at this temperature for 30 minutes, and 8.68 mmol (2.2 g) of iodine in 4 ml of anhydrous tetrahydrofuran was then added dropwise. After 30 minutes of stirring at this temperature, the reaction mixture was warmed to 23° C., and water was added carefully. The solvent was extracted with ethyl acetate and the combined organic phase was washed with sodium thiosulphate solution and saturated sodium chloride solution and dried over sodium sulphate. The solid obtained after distillative removal of solvent under reduced pressure was stirred with diisopropyl ether and yielded 1.55 g (68%) of 1-cyclopentyl-5-iodotetrazole with a melting point of 119° C.

The compounds listed in Table 1 were prepared analogously to Example 1:

TABLE 1

(Exemplary compounds of the formula 1)

| Example No. | R¹ | Physical data |
|---|---|---|
| 1 | cyclopentyl | m.p. = 119° C. |
| 2 | cyclohexyl | m.p. = 134° C. |
| 3 | 4-methylcyclohexyl | m.p. = 114° C. |
| 4 | 2-methylcyclohexyl | m.p. = 65° C. |
| 5 | 4-tert-butylcyclohexyl | m.p. = 153° C. |
| 6 | 4-cyclohexylcyclohexyl | m.p. = 168° C. |
| 7 | 4-(N-methyl-N-ethylamino)cyclohexyl | m.p. = 100° C. |
| 8 | 2,3-dimethylcyclohexyl | m.p. = 90° C. |
| 9 | 2-isopropylcyclohexyl | m.p. = 160° C. |
| 10 | 2,6-diisopropylcyclohexyl | m.p. = 152° C. |
| 11 | decahydronaphthyl | m.p. = 82° C. |
| 12 | 2-ethylcyclohexyl | m.p. = 66° C. |
| 13 | 4-ethylcyclohexyl | m.p. = 81-93° C. |
| 14 | 4-ethoxycyclohexyl | m.p. = 122-124° C. |
| 15 | 3-trifluoromethylcyclohexyl | m.p. = 116° C. |

TABLE 1-continued (Exemplary compounds of the formula 1)

| Example No. | R¹ | Physical data |
|---|---|---|
| 16 | | m.p. = 114° C. |
| 19 | | m.p. = 101° C. |
| 20 | | m.p. = 64° C. |
| 21 | | m.p. = 163° C. |

USE EXAMPLE A

To demonstrate the activity against fungi, the minimum inhibitory concentrations (MIC) of agents according to the invention were determined:

In each case, the active compounds according to the invention, in concentrations of from 0.1 mg/l to 5000 mg/l, were added to an agar which had been prepared using malt extracts. After the agar had solidified, it was contaminated with pure cultures of the test organisms listed in Table 3. The MIC was determined after 2 weeks of storage at 28° C. and 60 to 70% relative atmospheric humidity. The MIC is the lowest concentration of active compound at which there is no colonization by the microbial species used. The MIC values are indicated in Table 3 below.

TABLE 2

Minimum inhibitory concentrations (ppm) of compounds of the formula (I) according to the invention

| Example No. | Penicillium brevicaule | Chaetomium globosum | Aspergillus niger |
|---|---|---|---|
| 1 | <20 | <20 | <20 |
| 2 | <20 | <20 | <40 |
| 3 | <10 | <20 | <20 |

USE EXAMPLE B

To test dispersion coatings for resistance to mould, the following procedure was adopted:

The paint to be tested was applied to both sides of a suitable base. To obtain results which are close to practice, some of the test specimens were rinsed out with running water (24 h, 20° C.) before the test for mould resistance; others were treated with a current of warm fresh air (7 days, 40° C.).

The samples prepared in this way were then placed on an agar nutrient medium, and both samples and nutrient medium were contaminated with fungal spores. After 2-3 weeks storage (29±1° C., 80-90% rel. atmospheric humidity), the samples were compared.

The coating is considered to be permanently mould-resistant if the sample remains free from fungus or at most a slight border infestation can be detected.

For the contamination, fungal spores of the following mould fungi were used, which are known as paint destroyers or are frequently encountered on coatings:

*Alternaria tenuis*

*Aspergillus flavus*

*Aspergillus niger*

*Aspergillus ustus*

*Cindosporum herbarum*

*Paecilomyces variotii*

*Penicillium citrium*

*Aureobasidium pullulans*

*Stachybotrys chartarum*

Coatings according to recipe A are mould resistant (even after rinsing out and wind tunnel exposure) if they contain, for example, 1.0% (based on solids) of the compounds of Examples 2.

Recipe A:
Exterior dispersion paint based on Acroal 290 D (styrene acrylate)

| Trade name | Parts by weight | Chemical name |
|---|---|---|
| Bayer Titan RKB2 | 40 | Titanium dioxide |
| Talkum V58 new | 10 | Magnesium silicate, containing water |
| Durcal 5 | 45 | Calcite CaCO₃ |
| Walsroder MC 3000 S 2% | 30 | Methylcellulose |
| H₂O | 6.5 | Distilled water |
| Calgon N 10% | 3 | Polyphosphate |
| Pigmentverteiler A 10% | 1 | Polyacrylic acid salt |
| Agitan 281, 1:1 in Texanol | 1 | |
| White spirit | 5 | Mixture of aliph. hydrocarbons |
| Butyl glycol acetate | 1.5 | Butyl glycol acetate |
| Acronal 290 D (binder) | 71 | Polyacrylic acid ester |
| Total | 219 | |

Solids content 135.5 = 61.6%.

What is claimed is:

1. A compound of the formula (I)

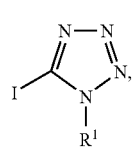

in which

R¹ represents cycloalkyl, its stereoisomers and any mixtures thereof.

2. The compound of the formula (I) according to claim 1, in which
$R^1$ represents optionally bridged $C_3$-$C_8$-cycloalkyl which is unsubstituted or mono- or polysubstituted by identical or different substituents,
where the substituents for the cycloalkyl radicals which are mono- or polysubstituted by identical or different substituents are selected from the group consisting of halogen; nitro; cyano; hydroxyl; unsubstituted $C_1$-$C_8$-alkyl; $C_1$-$C_8$-alkyl which is mono- to nonasubstituted by identical or different halogen substituents; $C_2$-$C_8$-alkynyl; unsubstituted $C_1$-$C_8$-alkoxy; $C_1$-$C_8$-alkoxy which is mono- to nonasubstituted by identical or different halogen substituents; unsubstituted $C_1$-$C_8$-alkylthio; $C_1$-$C_8$-alkylthio which is mono- to nonasubstituted by identical or different halogen substituents; $C_3$-$C_8$-cycloalkyl; amino; monoalkylamino having straight-chain or branched $C_1$-$C_8$-alkyl radicals; dialkylamino having identical or different straight-chain or branched $C_1$-$C_8$-alkyl radicals; $C_1$-$C_8$-acyl; $C_1$-$C_8$-acyloxy; $C_1$-$C_8$-alkoxycarbonyl; carboxyl; unsubstituted phenyl; and phenyl which is mono- to pentasubstituted by identical or different substituents from the group consisting of halogen, nitro, cyano, alkyl, haloalkyl, alkoxy, haloalkoxy, alkylthio, haloalkylthio, acyl, acyloxy, alkoxycarbonyl, carboxyl, amino, monoalkylamino and dialkylamino.

3. The compound of the formula (I) according to claim 1, in which
$R^1$ represents optionally bridged $C_3$-$C_8$-cycloalkyl which is unsubstituted or mono- to hexasubstituted by identical or different substituents,
where the substituents for the $C_3$-$C_8$-cycloalkyl radicals which are mono- to hexasubstituted by identical or different substituents are selected from the group consisting of fluorine; chlorine; bromine; iodine; nitro; cyano; hydroxyl; unsubstituted $C_1$-$C_6$-alkyl; $C_1$-$C_6$-alkyl which is mono- to hexasubstituted by identical or different substituents from the group consisting of fluorine, chlorine and bromine; $C_2$-$C_8$-alkynyl; $C_1$-$C_6$-alkoxy; $C_1$-$C_s$-alkoxy which is mono- to hexasubstituted by identical or different substituents from the group consisting of fluorine, chlorine and bromine; unsubstituted $C_1$-$C_6$-alkylthio; $C_1$-$C_6$-alkylthio which is mono- to hexasubstituted by identical or different substituents from the group consisting of fluorine, chlorine and bromine; $C_3$-$C_6$-cycloalkyl; amino; monoalkylamino having straight-chain or branched $C_1$-$C_6$-alkyl radicals; dialkylamino having identical or different straight-chain or branched $C_1$-$C_6$-alkyl radicals; $C_1$-$C_6$-acyl, $C_1$-$C_6$-acyloxy; $C_1$-$C_6$-alkoxy-carbonyl; carboxyl; unsubstituted phenyl; phenyl which is mono- to tetrasubstituted by identical or different substituents from the group consisting of fluorine, chlorine, bromine, iodine, nitro, cyano, hydroxyl, $C_1$-$C_4$-alkyl, $C_1$-$C_4$-haloalkyl which is mono- to pentasubstituted by identical or different substituents from the group consisting of fluorine, chlorine and bromine, $C_1$-$C_4$-alkoxy, $C_1$-$C_4$-haloalkoxy which is mono- to pentasubstituted by identical or different substituents from the group consisting of fluorine, chlorine and bromine, $C_1$-$C_4$-alkylthio, $C_1$-$C_4$-haloalkylthio which is mono- to pentasubstituted by identical or different substituents from the group consisting of fluorine, chlorine and bromine, $C_1$-$C_6$-acyl, $C_1$-$C_6$-acyloxy, $C_1$-$C_6$-alkoxycarbonyl, carboxyl, amino, monoalkylamino having straight-chain or branched $C_1$-$C_4$-alkyl radicals, and dialkylamino having identical or different straight-chain or branched $C_1$-$C_4$-alkyl radicals.

4. The compound of the formula (I) according to claim 1, in which
$R^1$ represents optionally bridged cyclopropyl, cyclobutyl, cyclopentyl, cyclohexyl, cycloheptyl, cyclooctyl, adamantyl, each of which is unsubstituted or mono- to tetrasubstituted by identical or different substituents,
where the cyclopropyl, cyclobutyl, cyclopentyl, cyclohexyl, cycloheptyl, cyclooctyl, adamantyl which are each optionally mono- to tetrasubstituted by identical or different substituents are selected from the group consisting of fluorine, chlorine, bromine, iodine, nitro, cyano, hydroxyl, methyl, ethyl, n-propyl, isopropyl, n-butyl, isobutyl, sec-butyl, tert-butyl, pentyl, hexyl, trifluoromethyl, ethynyl, propynyl, butynyl, pentynyl, hexynyl, methoxy, ethoxy, n-propoxy, isopropoxy, n-butoxy, isobutoxy, sec-butoxy, tert-butoxy, pentoxy, trifluoromethoxy, methylthio, ethylthio, n-propylthio, isopropylthio, trifluoromethylthio, cyclopropyl, cyclobutyl, cyclopentyl, cyclohexyl, amino, methylamino, ethylamino, n-propylamino, isopropylamino, dimethylamino, diethylamino, methylethylamino, di-n-propylamino, diisopropylamino, acetyl, acetyloxy, methoxycarbonyl, carboxyl, unsubstituted phenyl, phenyl which is mono- to trisubstituted by fluorine, chlorine, bromine, iodine, nitro, cyano, hydroxyl, methyl, ethyl, n-propyl, isopropyl, n-butyl, isobutyl, sec-butyl, tert-butyl, trifluoromethyl, methoxy, ethoxy, n-propoxy, isopropoxy, n-butoxy, isobutoxy, sec-butoxy, tert-butoxy, trifluoromethoxy, methylthio, ethylthio, n-propylthio, isopropylthio, trifluoromethylthio, formyl, acetyl, acetyloxy, methoxycarbonyl, ethoxycarbonyl, carboxyl, amino, methylamino, ethylamino, n-propylamino, isopropylamino, dimethylamino, diethylamino, methylethylamino, di-n-propylamino, and diisopropylamino.

5. A microbicidal composition, comprising at least one compound of the formula (I) according to claim 1 and at least one solvent or diluent.

6. A process for preparing a compound of the general formula (I) according to claim 1, comprising:
reacting iodine with
a tetrazole of the general formula (II)

(II)

in which
$R^1$ is cycloalkyl.

7. A composition comprising:
an industrial material; and
at least one compound of the formula (I) according to claim 1.

8. The composition according to claim 5, further comprising at least one processing auxiliary.

9. The composition according to claim 5, further comprising at least one further antimicrobially active compound.

10. The process according to claim 6, wherein said reacting is performed in the presence of a base or a diluent.

* * * * *